United States Patent
Isawa et al.

(10) Patent No.: US 7,084,331 B2
(45) Date of Patent: Aug. 1, 2006

(54) RICE CONTAINING ENDOPHYTIC BACTERIA AND METHOD OF PRODUCING IT

(75) Inventors: Tsuyoshi Isawa, Moriya (JP); Naoya Hiruma, Fujinomiya (JP); Takahiro Imada, Fujinomiya (JP); Munehiro Noda, Fujinomiya (JP); Yohsuke Kurihara, Fujinomiya (JP); Madoka Kon, Fujinomiya (JP)

(73) Assignees: Society for Techno-Innovation of Agriculture Forestry and Fisheries; Mayekawa Mfg. Co., Ltd., Tokyo (JP)

( * ) Notice: Subject to any disclaimer, the term of this patent is extended or adjusted under 35 U.S.C. 154(b) by 745 days.

(21) Appl. No.: 10/139,665

(22) Filed: May 2, 2002

(65) Prior Publication Data

US 2003/0135898 A1 Jul. 17, 2003

(30) Foreign Application Priority Data

Jan. 15, 2002 (JP) ............................. 2002-006534

(51) Int. Cl.
- A01H 5/00 (2006.01)
- C12N 1/12 (2006.01)
- C12N 1/20 (2006.01)
- C12N 15/01 (2006.01)

(52) U.S. Cl. ................. 800/320.1; 800/276; 435/252.1

(58) Field of Classification Search .................. None
See application file for complete search history.

(56) References Cited

U.S. PATENT DOCUMENTS

| | | | |
|---|---|---|---|
| 3,704,546 A * | 12/1972 | Hardy et al. | 47/58.1 R |
| 5,415,672 A | 5/1995 | Fahey et al. | 47/57.6 |
| 5,880,343 A | 3/1999 | Hiruma et al. | 800/320 |
| 5,914,107 A | 6/1999 | Hiruma et al. | 424/93.5 |
| 5,916,029 A | 6/1999 | Smith et al. | 47/57.6 |
| 6,180,855 B1 | 1/2001 | Hiruma et al. | 800/320 |
| 6,261,996 B1 | 7/2001 | Klittich et al. | 504/100 |
| 6,423,499 B1 * | 7/2002 | Song et al. | 435/6 |
| 2001/0032343 A1 | 10/2001 | Hiruma et al. | 800/320 |
| 2002/0040487 A1 | 4/2002 | Imada et al. | 800/278 |
| 2002/0142917 A1 * | 10/2002 | Triplett et al. | 504/117 |
| 2003/0195117 A1 | 10/2003 | Imada et al. | 504/117 |
| 2004/0116291 A1 * | 6/2004 | Triplett et al. | 504/117 |

OTHER PUBLICATIONS

Gopalaswamy Ganesan et al. The xylem of rice is colonized by *Azorhizobium caulinodans* Proceedings of the Royal Society Biological Sciences Series B vol. 267 No. 1439 Jan. 22, 2000 pp. 103-107.*

Reddy, P. et al. Rhizobia communication with rice roots: induction of phenotypic changes, mode of inveasion and extent of colonization. Plant Soil 194, 81-98 1997.*

Webster, G. et al. Interactions of rhizobia with rice and wheat. Plant Soil 194 p. 115-122 1997.*

Kirchof G. et al. Occurrence, physiological and molecular analysis of endophytic diazotrophic bacteria in gramineous energy plants Opportunites for biological nitrogen fixation in rice and other non-legumes. Plant and Soil 194L 45-55 1997.*

Ebeltagy et al. Endophytic Colonization and In Planta Nitrogen Fixation by a *herbaspirillum* sp. Isolated from Wild Rice Species. Applied and Environmental Microbiology, Nov. 2001 p. 5285-5293.*

Stolztful et al. Isolation of endophytic bacteria from rice and assessment of their potential for supplying rice wth biologically fixed nitrogen. Plant and Soil 194L 25-36 1997.*

Mehnaz, Samina et al. Isolation and 16S rRNA sequence analysis of the beneficial bacteria from the rhizosphere of rice. Canadian Journal of Microbiology 47(2): p. 110-117 Feb. 2001.*

Egener et al. Use of Green Fluorescent Protein to Detect Expression of nif Genes of *azoarcus* sp. BH72, a Grass-Associated Diazotroph, on Rice Roots Molecular Plant Microbe Interactions vol. 11, No. 1, 1998 pp. 71-75.*

(Continued)

*Primary Examiner*—Wendy Haas
(74) *Attorney, Agent, or Firm*—Morgan & Finnegan, L.L.P.; Kenneth H. Sonnenfeld; Michael A. Willis

(57) ABSTRACT

The present invention provides a rice plant that shows enhanced growth and increased seed production, which also enables reduction of the use of chemical fertilizers.

In the present invention, a nitrogen-fixing endophytic bacterium is isolated from bacteria symbiotically inhabiting natural plants, the isolated endophytic bacterium is artificially proliferated and then artificially inoculated into rice plants, and thus, the nitrogen-fixing endophytic bacteria are allowed to infect to rice plants.

12 Claims, No Drawings

OTHER PUBLICATIONS

Tirol-Padre et al. A Plant Sampling Procedure for Acetylene Reduction Assay to Detect Rice Varietal Differences in Ability to Stimulate N2 Fixation. Soil Biol. Biochem. vol. 20 No. 2 pp. 175-183 1988.*

Siddiqui, Z. A. and Mahmood, I., "Role Of Plant Symbionts In Nematode Management: A Review," *Bioresource Technology,* 54:217-226, 1995.

* cited by examiner

RICE CONTAINING ENDOPHYTIC BACTERIA AND METHOD OF PRODUCING IT

FIELD OF THE INVENTION

The present invention relates to a rice plant artificially infected with an endophytic bacterium and to a method for introducing an endophytic bacterium into a rice plant. In the present invention, rice plants include both cultivated rice, *Oryza sativa*, and wild rice, *Oryza officinalis*. Cultivated rice belongs to *Oryza sativa*, the genus *Oryza*, tribe *Oryzeae*, family Poaceae, and wild rice belongs to *Oryza officinalis*, the genus *Oryza*, tribe *Oryzeae*, family Poaceae.

BACKGROUND OF THE INVENTION

There are two rice varieties, lowland rice and upland rice. In Japan, 97% of rice plants are lowland rice grown in paddy fields. Cultivation and management of rice plants are conducted as follows: 35 to 50 days in a lowland nursery, 30 to 40 days from transplanting to heading, and 40 to 50 days from heading to harvest. It is said that about 10.5 kg of nitrogen is required for yielding 500 kg of unmilled rice, and 6.3 kg of nitrogen is taken up from soil and water, and the remaining 4.2 kg from fertilizers. Fertilizers used are mainly ammonium sulfate-based chemical fertilizers, and about 40% of the nitrogen applied is thought to be taken up and utilized. The remaining approximately 60% of the nitrogen is left in soil, and outflow of nitrogen into groundwater due to overuse of fertilizers and the influence of residual fertilizers on rivers and lakes have become social issues.

In nature, there are microorganisms called root nodule bacteria that fix nitrogen in the air and supply the nitrogen to plants. For example, *Rhizobium, Bradyrhizobium, Mesorhixobium*, and *Sinorhizobium* nodulate and reside in the roots of legumes, and take up nitrogen gas that accounts for four-fifths of the atmospheric air. They convert nitrogen into nitrogen compounds and supply them to plants. The root nodule bacteria of soybean belong to *Bradyrhizobium*.

Plants can be cultivated by delivering atmospheric nitrogen through such microorganisms, while maintaining the supply of nitrogen from the soil at a minimal level. These techniques are already being widely used, and seeds of plants, such as soybean, that are inoculated with root nodule bacteria are now commercially available. However, these techniques are not available for rice plants, since root nodule bacteria specifically infect legumes, but not poaceous plants.

SUMMARY OF THE INVENTION

As described above, the system using root nodule bacteria to convert atmospheric nitrogen into nitrogen compounds that are then supplied to plants is only used for legumes, and has not been applied to rice plants. Some natural wild plants symbiotically live with internal symbionts, endophytes. Endophytes inhabit plant tissues, particularly the so-called intercellular space, space between cells. Endophytes are divided broadly into two categories, fungi and bacteria. Some bacterial endophytes are engaged in nitrogen fixation. However, no bacterial endophyte that can fix nitrogen in the air and supply them to rice plants as efficiently as root nodule bacteria that infect legumes has been found so far in cultivated rice currently used, or in wild rice.

An objective of the present invention is to provide a rice plant created by artificially inoculating a bacterial endophyte-free rice plant with a bacterial endophyte, in particular, one that can fix nitrogen in the air, and a method for artificially introducing such an endophyte into a rice plant.

The present invention primarily relates to a rice plant created by artificially introducing an endophytic bacterium into a rice plant that is free of endophytic bacteria. In the present invention, the endophytic bacteria introduced into the rice plant may be a nitrogen-fixing endophytic bacterium. Furthermore, the endophytic bacteria introduced into the rice plant may be Herbaspirillum B502 FERM P-18563 (converted to accession number FERM BP-10395) or Azospirillum B510a FERM P-18564 (converted to accession number FERM BP-10447), which have been deposited in an international Patent Organism Depository. Accession number FERM BP-10395 was converted on Aug. 5, 2005 from accession number FERM P-18563, which was deposited on Oct. 18, 2001 at the National Institute of Advanced Industrial Science and Technology. Accession number FERM BP-10447 was converted on Nov. 9, 2005 from accession number FERM P-18564, which was deposited on Oct. 18, 2001 at the National Institute of Advanced Industrial Science and Technology. Rice plants into which an endophytic bacterium is introduced may be cultivated rice, *Oryza sativa*, or wild rice, *Oryza officinalis*.

The present invention relates to a method for introducing an endophytic bacterium into a rice plant, which comprises the steps of isolating and proliferating an endophytic bacterium inhabiting a plant, artificially inoculating a rice plant with the artificially proliferated endophytic bacteria, and infecting the rice plant with the artificially inoculated endophytic bacteria to form a symbiosis. In the present invention, the endophytic bacteria introduced into the rice plant may be Herbaspirillum B502 FERM P-18563 or Azospirillum B510a FERM P-18564, which have been deposited in an International Patent Organism Depository. Plants presumed to have endophytic bacteria may be homogenized and plated on a culture medium to isolate the bacteria. The isolated bacteria may be placed and sealed in containers having acetylene. A bacterium is selected by determining its nitrogen fixation activity by measuring the ethylene generated by the reduction of acetylene. DNA from the isolated bacterium may be amplified by PCR and the amplified DNA is subjected to a homology search to identify the bacterium. Furthermore, a foreign gene expressing an identifiable means may be introduced into the bacterium, and the identifiable means expressed from said foreign gene is used to identify whether the bacterium that infected the plant has colonized or not. Moreover, the plant inoculated with a bacterium to form a symbiosis may be placed and sealed in a container having acetylene, and the nitrogen-fixing ability of the plant into which the bacterium has been introduced may be evaluated by measuring the ethylene generated by the reduction of acetylene.

A preferred embodiment of the present invention relates to a rice plant into which an endophyte is artificially introduced, wherein the rice plant is one that was initially uninfected with any endophytes, or one that was made endophyte-free. In the present invention, an endophyte that is artificially introduced into a rice plant of family Poaceae is an endophytic bacterium engaged in nitrogen fixation. To achieve the present invention, such an endophyte is discovered by searching for symbiotic endophytes inhabiting plants growing in nature, evaluating the nitrogen fixation activity of the endophytes, and artificially introducing a selected endophyte into a plant.

Both endophytes, Herbaspirillum B502 (FERM P-18563; deposited in an International Patent Organism Depository) and Azospirillum B510a (FERM P-18564; deposited in an International Patent Organism Depositary), which were found and cultured by the present inventors, are endophytic bacteria having nitrogen-fixing ability. The present invention demonstrated that these endophytes can be introduced into a rice plant to form a symbiosis. Plants into which these endophytes can be introduced may be useful rice plants, including cultivated rice, Oryza sativa, wild rice, Oryza officinalis. Progenies of these rice plants may also be included in the present invention.

Next, a method for introducing an endophytic bacterium, i.e. an endophyte, into a rice plant is described. In the method, an endophyte forming a symbiosis with a plant found in nature is isolated and artificially proliferated. This endophyte is artificially inoculated into a rice plant, a member of the family Poaceae. Subsequently, the artificially inoculated endophyte is allowed to infect the rice plant and form a symbiosis, thereby introducing the endophyte into the rice plant.

In the present invention, either of the above-described endophytes, which have been deposited in an International Patent Organism Depositary, can be used for the artificial inoculation in the step of artificially inoculating the endophyte. In addition, the endophyte introduced into rice plants does not necessarily need to be one kind, and two or more different types of endophytes can be introduced simultaneously or separately.

Herbaspirillum sp. B502 and Azospirillum sp. B510a produced a large number of endotrophic bacteria when they were inoculated and made to colonize in wild rice Oryza officinalis, and cultivated rice Oryza sativa. They also exhibited high levels of acetylene reducing activity, demonstrating that nitrogen fixation was actually conducted in the wild rice Oryza officinalis and the cultivated rice Oryza sativa, to which endophytes were inoculated. Plant growth and seed yield were also enhanced. These results seem promising for reducing the amount of fertilizers applied in the current practice of rice agriculture, which uses chemically synthesized nitrogen sources, as well as for increasing the yield. Such reductions of chemical fertilizers may reduce the amount of fossil fuel required for producing these fertilizers. Although nitrogen is not washed away much in lowland paddy fields, reduction of chemical fertilizers may also reduce the outflow of surplus nitrogen into the environment caused by excessive application of fertilizers, lessening the burden on the environment and the cost of rice cultivation.

DETAILED DESCRIPTION OF THE INVENTION

As one embodiment of the present invention, introduction of an endophyte into a rice plant is described further in detail below, according to the steps of the procedure.

(1) Isolation and Culture of the Endophytes

Plants are screened and collected from nature. A piece of each plant is soaked in 70% ethanol for 30 minutes, subsequently in 2% sodium hypochlorite solution for five minutes to sterilize the surface of the plant piece. The plant piece is then homogenized in a mortar while adding sterilized saline and sea sand, followed by inoculation into Rennie's semi-solid medium in a test tube and incubation at 30° C. to isolate endophytes.

(2) Determination of Nitrogen Fixation Activity of the Endophytes

Since the nitrogen-fixing enzyme, nitrogenase, catalyzes the reduction of acetylene into ethylene, the acetylene reducing activity can be assessed as an index of nitrogenase activity. Therefore, the isolated endophytic bacterium was shut tight in a test tube, which is sealed by replacing the cap with a sterilized double rubber stopper and adding 5% (v/v) acetylene, and incubated in the dark for 24 hours at 25° C. Subsequently, the gas contained in the tube is removed and the generated ethylene is measured by gas chromatography to estimate the nitrogenase activity.

(3) Identification of the Endophytes

When the generation of ethylene is confirmed, the endophytic bacteria are identified by analyzing the 16s rRNA gene. Several forward-and reverse-primers corresponding to the internal region of the 16s rRNA gene are prepared, and a pair of forward-and reverse-primers is selected. The DNA solution extracted from the lysate of the bacterial isolate is used as template to elongate and amplify the DNA by PCR. The DNA fragment thus amplified is purified and the nucleotide sequence of the internal region of the 16s rRNA gene (about 1.5 kb in length) is determined after salt and primers are removed. Homology search for the nucleotide sequence is conducted using the DDBJ/GenBank/EMBL database. Subsequently, the phylogenetic relationship of the nucleotide sequences of the 16s rRNA gene is analyzed among the isolated endophytic bacteria, bacteria of genera and species that exhibit high sequence homologies to the isolated endophytic bacteria, and other wide varieties of bacterial genera and species, using ClastalW, a phylogenetic tree building program.

(4) Labeling of the Endophytes

Apart of the endophytes whose species was identified is labeled with GFP to confirm the infection after they are inoculated into a plant. GFP (Green Fluorescent Protein) is a protein that was isolated from jellyfish (Aequoria victoria), which emits a green fluorescent light when exposed to blue or ultraviolet light. The gene producing GFP, the gfp gene, is introduced. The pUTgfpx2 plasmid that contains a mini-transposon comprising two gfp genes and a kanamycin resistance gene in the pUT plasmid that is able to replicate only in enteric bacteria, is introduced into the bacteria by electroporation.

(5) Introduction of the Endophytes

The endophytic bacteria are cultured in the NB medium. Cells in the exponential phase are collected by centrifugation at 8,000G (G: gravitational acceleration) for 1 minute, suspended in physiological saline, and re-collected by centrifugation. This washing step is repeated three times. After washing, the cells are resuspended in physiological saline to a concentration of $2\times10^7$ cells/ml. The cell suspension is inoculated onto surface-sterilized seeds by overlaying the seeds with 50 µl ($1\times10^6$ cells/ml) of the suspension per seed.

(6) Confirmation of the Introduction

Endophyte infection can be confirmed by observing a tissue piece of the gfp gene-introduced plant using fluorescence microscopy. Additionally, endophytes can be isolated by sterilizing the surface of the tissue and placing it on NB medium.

(7) Determination of the Nitrogen-Fixation Activity of the Plants

The rice plant is placed in an air-dryer and dried at 80° C. for three days. Then, the plant is ground and the powder is gasified in nitrogen gas in a quartz crystal tube by the combustion method. The generated gas is analyzed using an RMI-2 mass spectrometer to determine 15-N%.

A primary feature of the present invention relates to a rice plant produced by introducing an endophytic bacterium into a rice plant having no endophytic bacteria, and a method for introducing the endophytic bacteria into a rice plant.

Accordingly, growth and seed production of the rice plant are enhanced through the nitrogen fixation conducted by the bacterium introduced into the rice plant. The present invention is promising for reducing fertilizers and increasing yield of crops when it is applied to cultivated rice. Reduction of the use of chemical fertilizers will enable the alleviation of the burden on the environment and cost reduction in rice farming.

EXAMPLES (1) Isolation of Nitrogen-fixing Endophytes from Rice

Poaceous plants growing naturally on soil were appropriately collected. They were cut into small pieces and soaked in 70% ethanol for 30 seconds, and subsequently in 2% sodium hypochlorite solution for five minutes to sterilize the surfaces. The plant pieces were then homogenized using a mortar while adding sterilized saline and sea sand. The homogenates were inoculated into Rennie's semi-solid medium in test tubes and incubated at 30° C.

Acetylene reduction activity was determined for tubes that produced bacteria. Turbid portions or pellicles in the medium in tubes that exhibited acetylene reduction activity were collected by a pipette, and serially diluted from $10^{-1}$ to $10^{-9}$ concentrations with physiological saline. Each of the diluted cell suspensions was re-inoculated into Rennie's semi-solid medium in tubes and incubated. Rennie's medium is known to allow the proliferation of all known nitrogen-fixing bacteria, but it also allows other bacterial species to grow. Therefore, fractions with lower serial dilutions may contain more bacteria belonging to species other than nitrogen-fixing species. Thus, among the tubes in which bacteria grew and the acetylene reducing activity was detected, tubes containing the most diluted fractions were selected, and single colonies were isolated from the turbid portions or pellicles in the tubes that were plated on Rennie's agar medium. Colonies that exhibited acetylene reduction activity were selected from the single colonies observed.

(2) Introduction of the Endophytes 16s rRNA regions were elongated and amplified by PCR and their nucleotide sequences were determined. Several forward-and reverse-primers corresponding to the internal region of the 16s rRNA gene were prepared, and a pair of forward-and reverse-primers was selected and used for PCR. PCR was performed using, as template, DNA extracted from the endophytic bacterial cell lysate. The amplified DNA fragments were purified and sequenced after salt and primers were removed. The nucleotide sequence of the internal region of the 16s rRNA gene, about 1.5 kb in length, was determined.

Homology search for the determined nucleotide sequence was conducted using the DDBJ/GenBank/EMBL database. Subsequently, the phylogenetic relationship of the nucleotide sequence of the 16s rRNA gene was analyzed among the isolated endophytic bacteria, bacteria of the genera and species that exhibit high sequence homologies to the isolated endophytic bacteria, and other wide varieties of bacterial genera and species, using the ClastalW W phylogenetic tree building program. The result revealed that the isolates B502 and B510a belong to genera Herbaspirillum and Azospirillum, respectively.

(3) Generation of a Labeled Isolate of B502

Since it is difficult to observe bacteria in plant tissues, a gene producing a fluorescent protein was introduced into the bacterium. GFP (Green Fluorescent Protein) is a protein that was isolated from jellyfish (*Aequoria victoria*). This protein emits a green fluorescent light when exposed to blue or ultraviolet light. The gene for this GFP, gfp, was isolated and used for labeling the isolated bacterium. Plasmid pUTgfpx2 is based on the pUT plasmid that is able to replicate only in enteric bacteria, and contains a minitransposon comprising two gfp genes and a kanamycin resistance gene. This plasmid was introduced into Herbaspirillum sp. B502 by electroporation, and a kanamycin resistant bacterium was isolated. This bacterium was exposed to light at around 500 nm, and emission of fluorescent light was confirmed.

(4) Culture of the Isolated Bacterial Strains

Herbaspirillum sp. B502 and Azospirillum sp. B510a were cultured in a similar manner. A single colony of each strain was plated on NB medium and incubated at 30° C. while shaking.

(5) Inoculation into Rice Plants

1. Inoculation by Bacterial Cell Adhesion to the Seeds

The bacteria were cultured on NB medium, and the cells in the exponential phase were collected by centrifugation at 8,000G (G: gravitational acceleration) for 1 minute. The cells were suspended in physiological saline and re-collected by centrifugation. This step was repeated three times for washing. After washing, the cells were resuspended in physiological saline to a concentration of $2 \times 10^7$ cells/ml. Seeds of wild rice, *Oryza officinalis* and cultivated rice, *Oryza sativa*, were dehulled and subjected to surface sterilization as follows: the seeds were soaked in 70% ethanol for a few seconds, washed with sterilized water at once, and soaked in 0.5% sodium hypochlorite solution for thirty seconds while shaking. The seeds were washed ten times by shaking the culture in sterilized water for 15 minutes. Surface-sterilized seeds were placed on a soft agar-water culture solution for rice in a plant box or test tube. The seeds were inoculated with the bacteria by applying 50 μl ($1 \times 10^6$ cells/ml) of the cell suspension per seed.

2. Slit Inoculation

Seeds of wild rice, *Oryza officinalis*, and cultivated rice, *Oryza sativa*, were dehulled, and soaked in 70% ethanol for a few seconds. Then, they were washed with sterilized water and then soaked in 2.5% sodium hypochlorite solution for 20 minutes for surface sterilization. The seeds were washed three times with sterilized water. The surface-sterilized rice seeds were placed on an agar medium and allowed to germinate by incubating at 28° C. for 2 to 4 days in the dark.

The bacterial cells were cultured in NB medium and collected at their exponential phase by centrifugation for ten minutes at 3,000 rpm. The cells were suspended in physiological saline and re-collected by centrifugation. This step was repeated three times for washing. The rinsed cells were resuspended in physiological saline to a concentration of $1.0 \times 10^6$ cells/ml.

Seedlings that were cultivated and made to germinate in advance were cut with a scalpel in the vicinity of the meristem to make a slit. Bacterial cells were inoculated into the plants through the scalpel loaded with an appropriate amount of bacterial cells suspended in physiological saline. After the inoculation, the seedlings were placed on a soft agar-water culture medium for rice in test tubes.

(6) Propagation of the Rice Plants to Which Endophytes were Infected

1. Cultivation in Plant Boxes or Test Tubes

Soft agar-water culture medium for rice was placed in plant boxes or test tubes. Wild rice *Oryza officinalis* and cultivated rice *Oryza sativa*, to which Herbaspirillum sp. B502 and Azospirillum sp. B510a were inoculated, were incubated on the medium at 25° C. in the light for 16 hours and in the dark for 8 hours. The rice seedlings were allowed to aseptically grow for 10 to 14 days.

2. Water Culture With Wagner's Pots

The rice seedlings grown in plant boxes were transplanted into 1/5000 a Wagner's pots containing water culture medium for rice and were grown until maturity in the light for 11 hours at 28° C. and in the dark for 13 hours at 22° C. until they matured.

(7) Confirmation of Infection

1. Confirmation of Infection by Fluorescence Microscopy

Seedlings of wild rice *Oryza officinalis* and cultivated rice *Oryza sativa*, to which the gfp mutant of Herbaspirillum sp. B502 were inoculated, were examined by a fluorescence stereomicroscope. Furthermore, leaf blades of the seedlings of wild rice *Oryza officinalis* were observed by a cofocal laser microscope to verify where in the rice tissue colonization of the bacteria occurred. As a result, a large number of the gfp mutant of Herbaspirillum sp. B502 was observed to colonize both aerial and subterranean parts of the wild rice *Oryza officinalis*. This mutant was also observed to mainly colonize the subterranean part of the cultivated rice *Oryza sativa*, although the number of bacteria was smaller than that found in the wild rice *Oryza officinalis*. The results also revealed that colonization of the gfp mutant of Herbaspirillum sp. B502 occurs in the intercellular space of the wild rice *Oryza officinalis*.

The wild rice *Oryza officinalis* and the cultivated rice *Oryza sativa*, to which the gfp mutants of Herbaspirillum sp. B502 were inoculated, were grown to maturity. Rice plants at the heading stage and flowering stage were divided into four parts, i.e. root, sheath, leaf blade, and panicle. Each part was homogenized as described above and plated on NB agar medium to examine the ability of the bacterium to colonize the rice tissue. The result revealed that a large number of the gfp mutant of Herbaspirillum sp. B502 colonized the rice plants, mainly at the root, stem, and leaf sheath, even at the middle and late stages of growth.

2. Confirmation of Infection by Isolation

Rice plants, to which bacteria were inoculated, were cultivated for 10 to 14 days, and the whole seedlings were surface sterilized by soaking in 70% ethanol for a few seconds and subsequently in 1% sodium hypochlorite solution for 30 seconds. Then, the plantlets were homogenized in a sterilized mortar while adding sterilized saline and sea sand. The homogenates were plated on NB agar medium. Colonies formed on the medium were counted to examine the ability of the inoculated bacteria to colonize the plant tissue. As a result, endophytes were isolated, among which Herbaspirillum sp. B502 was shown to colonize both wild rice *Oryza officinalis* and cultivated rice *Oryza sativa*, and Azospirillum sp. B510a to colonize cultivated rice *Oryza sativa*.

(8) Examination of the Nitrogen-Fixing Ability of the Inoculated Bacteria

1. Evaluation of the Nitrogen-Fixing Ability by Acetylene Reduction Method

Since the nitrogen-fixing enzyme, nitrogenase, catalyzes the reduction of acetylene into ethylene, acetylene reducing activity can be assessed as an index of nitrogenase activity. Wild rice *Oryza officinalis* and cultivated rice *Oryza sativa*, to which Herbaspirillum sp. B502 were inoculated, and cultivated rice *Oryza sativa*, to which Azospirillum sp. B510a were inoculated, were cultured in test tubes for 10 days. Mock-inoculated rice plants were used as controls.

The caps of the test tubes were replaced with autoclave-sterilized double rubber stoppers to seal up the tubes. Subsequently, 5% (v/v) acetylene was added to the tubes and incubated in the dark for 24 hours at 25° C. After the incubation, the gas was removed from the tubes and subjected to gas chromatography to measure the ethylene generated. Thereby, nitrogenase activity was estimated. As a result, acetylene-reducing activity was observed in all three combinations. Accordingly, it was shown that the inoculated bacteria colonize rice plants and exhibit a nitrogenase activity. The activity was highest in wild rice *Oryza officinalis* to which Herbaspirillum sp. B502 was inoculated followed by cultivated rice *Oryza sativa* to which Azospirillum sp. B510a was inoculated and then by cultivated rice *Oryza sativa* to which Herbaspirillum sp. B502 was inoculated.

Wild rice *Oryza officinalis* and cultivated rice *Oryza sativa* to which Herbaspirillum sp. B502 were inoculated were aseptically cultivated in plant boxes for 14 days. The rice plants were collected, surface sterilized by soaking in 1% sodium hypochlorite solution for 30 seconds, and placed in vials. The vials were sealed with stoppers, charged with acetylene as described above, and incubated. Acetylene-reducing activity was measured for each vial. The results revealed that rice plants, to which the bacteria were inoculated, exhibited acetylene-reducing activity. These results were similar to those described above, demonstrating that the inoculated bacteria that colonized within the plant, instead of the surface of the plant, are responsible for the acetylene-reducing activity.

2. Evaluation of the Nitrogen-Fixing Ability with N-15

Rice plants were sampled and dried for three days at 80° C. in a circulating air dryer. After having been ground, the powder of the plants was nitrogen-gasified in a quartz crystal tube using the combustion method. The gas was analyzed using an RMI-2 mass spectrometer to determine 15-N%. The results were compared with those obtained from the mock-inoculated plants (free of the gfp mutant of Herbaspirillum sp. B502), and extent of the replacement of 15-N with 14-N was examined to assess the nitrogen-fixing ability of the inoculated bacteria.

Wild rice *Oryza officinalis* and cultivated rice *Oryza sativa* both inoculated with Herbaspirillum sp. B502 were transplanted into 1/5000 a Wagner's pots. They were cultivated, using an environment control system, until maturity under the following conditions: under light for 11 hours at 30° C. and in the dark for 13 hours at 24° C. During the cultivation to the heading stage, ammonium nitrate in which both nitrate and ammonium forms of nitrogen was substituted with heavy nitrogen (99.3 atom %) was used as the nitrogen source in the rice water culture solution.

A nitrogen-free water culture solution was used during about one month from the heading to maturing stages, and during this period, the dilution rate of the heavy nitrogen in the rice plant with nitrogen from nitrogen sources other than the culture solution, such as atmosphere, namely the NDFA % (nitrogen derived from other sources such as seed and air) was determined. The dilution rate was compared between inoculated and non-inoculated plots, and nitrogen fixation by the inoculated bacteria was examined. As a result, it was shown that NDFA % was significantly increased in the inoculated plot in the cultivated rice *Oryza sativa*. This showed that rice plants in which the inoculated bacteria colonized conducted nitrogen fixation even in the middle and late stages of their growth. Difference in plant growth was also observed between the plots, and plants of the inoculated plots showed enhanced growth and increased seed production.

The invention claimed is:

1. A rice plant produced by artificially introducing an endophytic bacterium into a rice plant that is free of endophytic bacteria, wherein said introduced endophytic bacteria is Herbaspirillum FERM BP-10395 or Azospirillum FERM BP-10447, which have been deposited in the National Institute of Advanced Industrial Science and Technology.

2. The rice plant of claim 1, wherein said introduced endophytic bacteria is engaged in nitrogen fixation for the rice plants.

3. The rice plant of claim 1, wherein said rice plant, into which an endophytic bacterium is introduced, is cultivated rice *Oryza sativa* or wild rice *Oryza officinalis*.

4. An isolated bacterium selected from the group consisting of a bacterium deposited as accession number FERM BP-10395 and a bacterium deposited as accession number FERM BP-10447, both deposited at the National Institute of Advanced Industrial Science and Technology.

5. A method for introducing an endophytic bacterium into a rice plant, comprising the following steps of:
   isolating and proliferating an endophytic bacterium which inhabits a plant;
   artificially inoculating the artificially proliferated endophytic bacteria into the rice plant; and
   infecting the rice plant with the artificially inoculated endophytic bacteria to form a symbiosis, wherein said introduced endophytic bacteria is Herbaspirillum FERM BP-10395 or Azospirillum FERM BP-10447, which have been deposited in the National Institute of Advanced Industrial Science and Technology.

6. The method of claim 5, wherein said plant presumed to form a symbiosis with a bacterium is homogenized and plated on a medium for culturing and isolating the bacterium.

7. The method of claim 5, wherein said isolated bacterium is placed and sealed up in a container having acetylene and the bacterium is selected by determining the nitrogen fixation activity of the isolated bacterium by measuring ethylene generated by the reduction of acetylene.

8. The method of claim 5, wherein DNA from the isolated bacterium is amplified by PCR and homology search is performed for the amplified DNA to identify the bacterium.

9. The method of claim 5, wherein a foreign gene expressing an identifiable means is introduced into said bacterium, wherein said identifiable means expressed from said foreign gene is used to identify whether said bacterium has colonized.

10. The method of claim 5, wherein the rice plant into which the bacterium is inoculated to form a symbiosis is placed and sealed in a container having acetylene and the ability of said plant to fix nitrogen is evaluated by measuring ethylene generated by the reduction of said acetylene.

11. The method of claim 5, wherein said inoculation is performed by inoculation comprising bacterial cell adhesion to seeds.

12. The method of claim 5, wherein said inoculation is performed by inoculation comprising penetration of seeds.

* * * * *